United States Patent
Kawde et al.

(10) Patent No.: US 9,182,367 B2
(45) Date of Patent: Nov. 10, 2015

(54) ELECTROANALYTICAL METHOD FOR DETERMINATION OF PHENOLS

(71) Applicant: KING FAHD UNIVERSITY OF PETROLEUM AND MINERALS, Dhahran (SA)

(72) Inventors: Abdel-Nasser Metwally Aly Kawde, Dhahran (SA); Mohamed Aly Morsy, Dhahran (SA); Nurudeen A. Odewunmi, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 14/242,844

(22) Filed: Apr. 1, 2014

(65) Prior Publication Data

US 2015/0276646 A1 Oct. 1, 2015

(51) Int. Cl.
*G01N 27/28* (2006.01)
(52) U.S. Cl.
CPC .................................. *G01N 27/28* (2013.01)
(58) Field of Classification Search
CPC ......... C12H 1/22; G01N 17/02; G01N 27/26; G01N 27/283; G01N 33/487; G01N 33/146; G01N 33/18; G01N 27/28; C25B 3/02; C25B 11/04
See application file for complete search history.

(56) References Cited

U.S. PATENT DOCUMENTS

2009/0071823 A1*  3/2009  Catt et al. ................. 204/403.04
2009/0294298 A1* 12/2009  Compton et al. ............ 205/437
2010/0012529 A1*  1/2010  Kauffman .................... 205/787

OTHER PUBLICATIONS

Ezerskis et al., 2001, Pure Appl Chem vol. 73, No. 12, 1929-1940.*
Compton et al. (Analyst, 2014, 139, 5911-5918).*
Adam et al. (Sensors 2007, 7, 2402-2418).*
Cyclic Voltammetry I, 1999.*
Ti et al. (Talanta 55 (2001) 1205-1210).*
Zoulis et al. (Analytica Chimica Acta 320 (1996) 255-261).*
Beltagi et al. (American Journal of Analytical Chemistry vol. 4 No. 4, 2013).*
Al-Ghamdi et al. Chemistry Central Journal 2012, 6:15.*
Sun, Dong et al., "Electrochemical Determination of 2-chlorophenol using an acetylene black film modified glassy carbon electrode", Water Research, 2006, vol. 40, pp. 3069-3064.
Wang Joseph, Stable and Sensitive electrochemical Detection of Phenolic Compounds at Carbon Nanotube Modified Glassy Carbon Electrodes, Electroanalysis, 2003, vol. 15, pp. 1830-1834.
Enache Adrian Teodor et al., "Phenol and para-substituted phenols electrochemical oxidation pathways", J. of Electroanalytical Chemistry, 2011, vol. 655, pp. 9-16.

* cited by examiner

*Primary Examiner* — Jennifer Dieterle
(74) *Attorney, Agent, or Firm* — Richard C. Litman

(57) ABSTRACT

The electroanalytical method for determination of phenols is a method for determining the concentration of phenolic compounds and their chloro-derivatives, on the surface of a glassy carbon electrode (GCE) by cyclic voltammetry (CV) and/or square-wave stripping voltammetry (SWASV) using a redox active polymer film that is formed on the surface of the GCE when the electro-polymerization potential is reached. The electroanalytical method comprises contacting an aqueous sample containing a phenolic compound(s) with an electrode assembly having a working electrode; generating a voltammogram of the analyte by varying an applied accumulation potential or applied potential, and measuring the size of voltammogram peaks corresponding to a redox-active polymeric film that develops at the working electrode at the electropolymerization potential in order to determine the concentration of the phenolic compound.

11 Claims, 9 Drawing Sheets

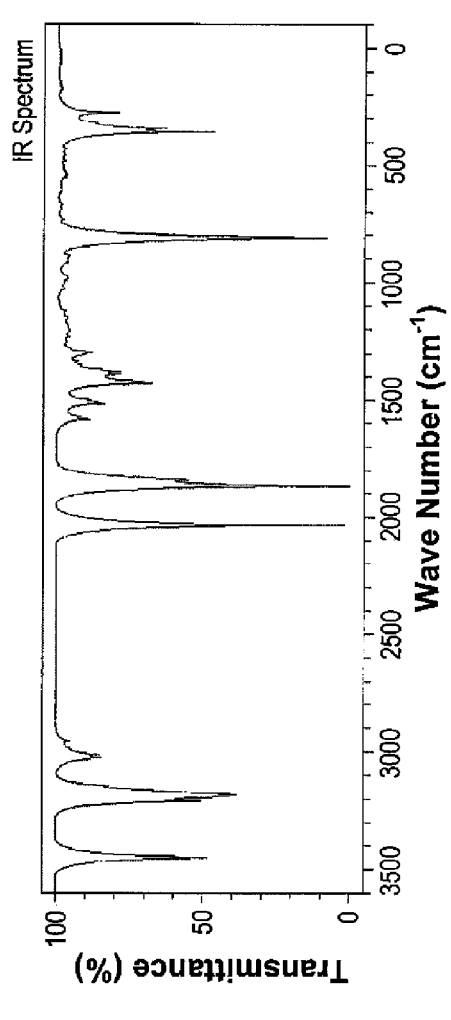
Fig. 4A
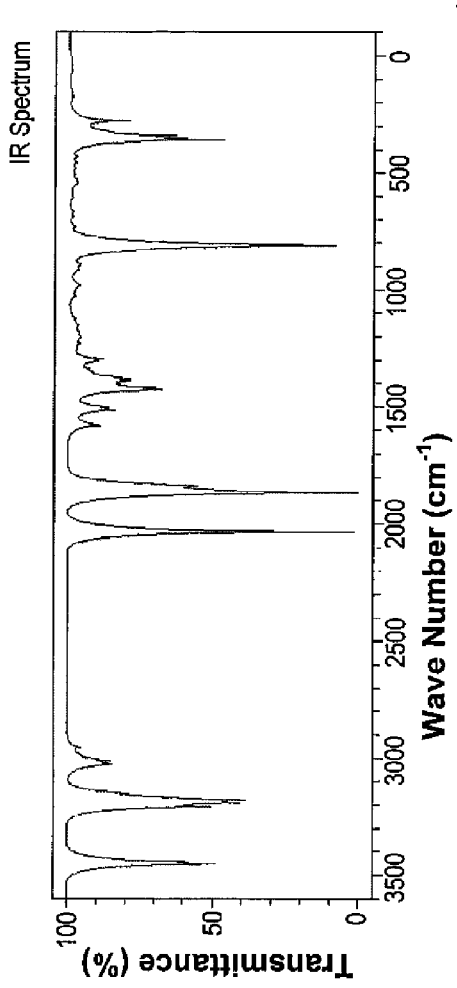
Fig. 4B
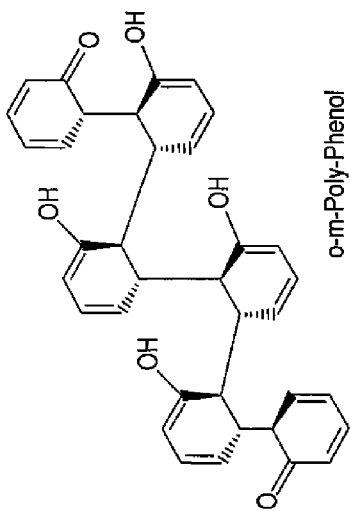

ELECTROANALYTICAL METHOD FOR DETERMINATION OF PHENOLS

BACKGROUND OF THE INVENTION

1. Field of the Invention

The present invention relates to electroanalytical methods, and particularly to an electroanalytical method for determination of phenols by cyclic voltammetry (CV) and square wave stripping voltammetry (SWASV).

2. Description of the Related Art

There is considerable interest in the determination of phenolic compounds in industrial, environmental or food samples. Additionally, detection of phenolic compounds is of considerable importance owing to their presence in a broad range of disinfectants. Chlorophenols (hereinafter, CPs), which are phenolic compounds, are ubiquitous and affect several organs in humans, and therefore CPs are considered to be a serious problem due to their known toxicity at low concentration levels. Thus, the analytical determination of CPs is of great interest in the field of environmental protection, as well as industrial process control.

Various analytical techniques have been described for determining CPs. These include chromatographic, spectrophotometric and electroanalytical methods. The chromatographic techniques, however, take longer time for separation before detection and/or need efficient compatible mobile phases with the stationary phase, and therefore consume a lot of reagents, and may even lead to environmental pollution. Similarly, the spectrophotometric methods are easily disturbed by turbidity and the color of detected components. In view of the drawbacks of the foregoing methods, electroanalytical methods for determination of phenol have attracted considerable interest, owing to their simplicity, speed, convenience and low cost. However, electroanalytical studies have shown that the electrochemical oxidation of phenols at various types of solid electrodes leads to a remarkable lowering in the phenol's oxidation rate, namely, the phenomenon of "electrode fouling" due to the low permeability and strong adhesion of a layer (film) that is formed at the electrode surface.

Moreover, it appears that in previous studies, the primary oxidation peak of phenol, which is obtained at a mild accumulation potential (+400 mV), was the only peak that was used in the electrochemical investigation and analytical determination of 2-chlorophenol when using an acetylene black film-modified glassy carbon electrode. Other phenol polymerization peaks that may be produced due to redox polymerization of phenolic compounds were never considered for any analytical investigation of phenols. Their fouling effects were considered as obstacles toward sensing of the phenolic compounds. As such, present electroanalytic methods so far have not addressed the use of the formed phenol-polymeric film that occurs during electrode fouling for a more sensitive, facile, and direct electroanalytical determination of CPs at unmodified glassy carbon electrode (hereinafter GCE) surfaces.

Thus, an electroanalytical method for determination of phenols solving the aforementioned problems is desired.

SUMMARY OF THE INVENTION

The electroanalytical method for determination of phenols is a method for determining the concentration of phenolic compounds and their chloro-derivatives, on the surface of a glassy carbon electrode (GCE) by cyclic voltammetry (CV) and/or square-wave stripping voltammetry (SWASV) utilizing a redox active polymer film that is formed on the surface of the GCE when the electro-polymerization potential is reached. The electroanalytical method comprises contacting an aqueous sample containing a phenolic compound(s) with an electrode assembly having a working electrode; generating a voltammogram of the analyte by varying an applied accumulation potential or applied potential, and measuring the size of voltammogram peaks corresponding to a redox-active polymeric film that develops at the working electrode at the electro-polymerization potential in order to determine the concentration of the phenolic compound.

The method further comprises the steps of preparing calibration curves for the redox-active polymeric film voltammogram peaks for known concentrations of the phenolic compound(s), and extrapolating the measured size of the analyte's voltammogram peaks against the calibration curve to determine the concentration of the phenolic compound(s) in the analyte.

These and other features of the present invention will become readily apparent upon further review of the following specification and drawings.

BRIEF DESCRIPTION OF THE DRAWINGS

FIG. 4A shows a structural formula of phenol and the corresponding predicted IR-spectra using AM1-semiempirical level of computation in Gaussian 03 W.

FIG. 4B shows a structural formula of an ortho-meta carbon-carbon coupled phenol polymer and the corresponding predicted IR-spectra using AM1-semiempirical level of computation in Gaussian 03 W.

Similar reference characters denote corresponding features consistently throughout the attached drawings.

DETAILED DESCRIPTION OF THE PREFERRED EMBODIMENTS

Figure 1A:
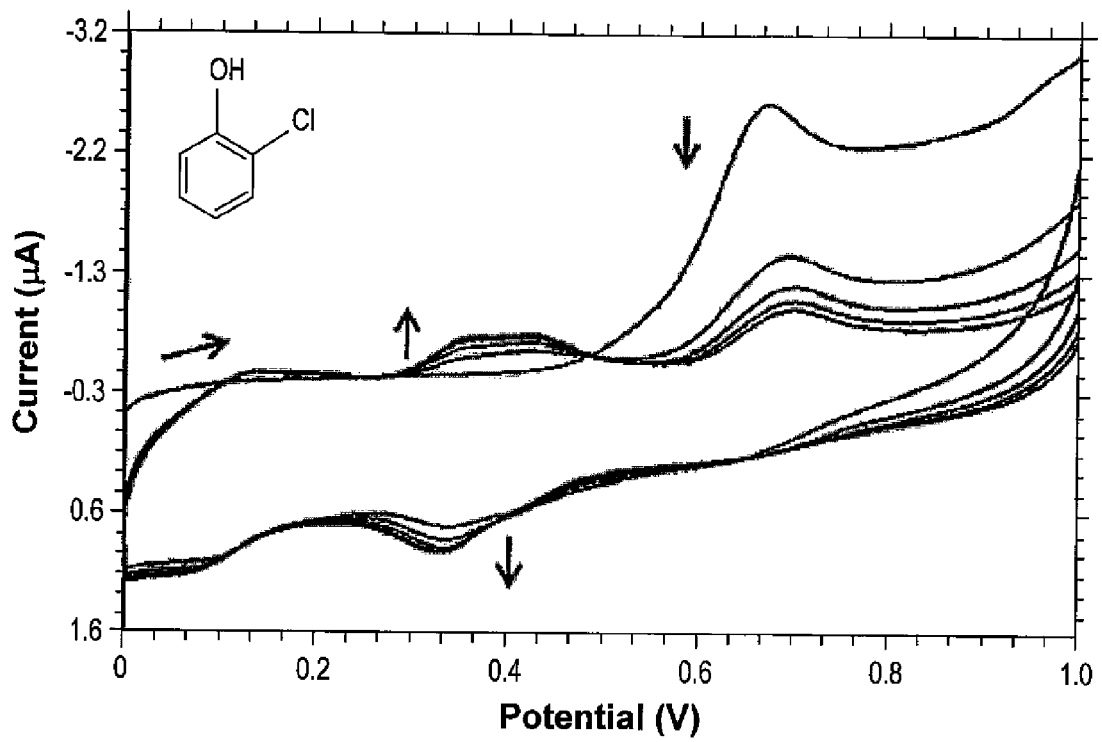
FIG. 1A is a cyclic voltammogram (CV) of five successive scans of 2-chlorophenol (30 µM) obtained in a phosphate buffer at (0.1 M, pH 7.0) at an accumulation potential of +400 mV, accumulation time of 60 seconds, and at a scan rate of 100 mV/s.

The electroanalytical method for determination of phenols is a method for determining the concentration of phenolic compounds, such as chlorophenols and their derivatives, on the surface of a glassy carbon electrode (GCE) by cyclic voltammetry (CV) and/or square-wave stripping voltammetry (SWASV) using a redox active polymer film that is formed on the surface of the GCE when the electro-polymerization potential is reached. The electroanalytical method comprises contacting an aqueous sample containing a phenolic compound(s) with an electrode assembly having a working electrode; generating a voltammogram of the analyte by varying an applied accumulation potential or applied potential, and measuring the size of voltammogram peaks corresponding to a redox-active polymeric film that develops at the working electrode at the electro-polymerization potential in order to determine the concentration of the phenolic compound.

The method further comprises the steps of preparing calibration curves for the redox-active polymeric film voltammogram peaks for known concentrations of the phenolic compound(s), and extrapolating the measured size of the analyte's voltammogram peaks against the calibration curve to determine the concentration of the phenolic compound(s) in the analyte.

The electroanalytical method for determination of phenols (i.e., phenol and its derivatives) is based upon voltammetric analysis of an aqueous sample of phenolic compounds. The method utilizes the phenol-electrode passivation or "fouling" effect for more sensitive and facile electroanalytical determination of phenolic compounds, such as chlorophenol and its derivatives. The common characteristic of all voltammetric techniques is that they involve the application of a potential (E) to a working electrode and the monitoring of the resulting current (I) flowing through the electrochemical cell. In many cases the applied potential is varied or the current is monitored over a period of time (t) as a function of the applied potential (E). Thus, all voltammetric techniques can be described as some function of E, I, and t. The electrochemical cell where the voltammetric experiment is carried out consists of a working (indicator) electrode, a reference electrode, and usually a counter (auxiliary) electrode. The reduction or oxidation of a substance at the surface of a working electrode at the appropriate applied potential results in the mass transport of new material to the electrode surface and the generation of a current (I).

In accordance with the present method, voltammetric measurements were performed with an electrochemical workstation (CHI1140A, CH Instruments Inc., Austin, Tex., USA) with a glassy carbon electrode (GCE) as a working electrode, Ag/AgCl as reference electrode (3M KCl, CHI111, CH Instruments Inc.) and platinum wire as counter electrode (CHI115, CH Instruments Inc.), which were inserted into a 3.0 ml glass cell through holes in its Teflon cover. The working electrode maybe a microelectrode or a macroelectrode. Prior to use, the GCE surface was polished with 0.1 µm and 0.05 µm gamma alumina powder and rinsed thoroughly with deionized water, Voltammetric measurements were conducted in phosphate buffer solution 0.1 M at a pH 7.0, or as otherwise mentioned in the appropriate Examples.

In accordance with the present method, cyclic voltammetry (hereinafter, CV) is used to perform voltammetric measurements where the potential from an initial potential (E1) to a final potential (E2) is varied over time through a complete cycle. CV is based on varying the applied potential at a working electrode in both forward and reverse directions (at some scan rate) while monitoring the current. FIG. 1 illustrates a cyclic voltammetric analysis of a typical phenolic compound, 2-chlorophenol, demonstrating both oxidation and reduction peaks thereof.

In accordance with the present method, square-wave adsorptive stripping voltammetry (hereinafter SWASV), is used to detect and determine the concentration of the phenolic compounds. SWASV involves adsorption of the analyte on the electrode surface, which is quantified by scanning or applying a square wave scan in the negative or positive direction to give a peak-shaped voltammetric response with amplitude proportional to the concentration. The excitation signal in square-wave voltammetry consists of a symmetrical square-wave pulse of amplitude Esw superimposed on a staircase waveform of step height ΔE, where the forward pulse of the square wave coincides with the staircase step. The differential current (difference between the forward and reverse currents centered on the redox potential) is then plotted as a function of potential, and the reduction or oxidation of species is measured as a peak or trough. The peak height is directly proportional to the concentration of the electroactive species. Direct detection limits down to the nanomolar concentrations are possible. Square-wave voltammetry provides several advantages because of its excellent speed, enhanced sensitivity and the rejection of background currents. Therefore, it is possible to control the rate of oxidation and reduction (redox) reactions of phenolic compounds by varying the applied accumulation potential in SWASV. FIG. 2 illustrates a representative SWASV analysis of a typical phenolic compound, 2-chlorophenol, demonstrating the oxidation peak thereof.

In the examples described below, a Nicolet 6700-FT-IR spectrometer equipped with attenuated total reflectance (ATR)-Smart Orbit module was used for FT-IR measurements. As with all FT-IR measurements, an infrared background was collected using a cleaned ATR crystal before any measurements. A piece of tissue soaked in alcohol or acetone is used to clean the ATR crystal before sample presentation. For phenol and poly-oxy-phenylene, the sample placed onto the crystal and covered/pressed using the pressure arm positioned over the crystal/sample area. For the ATR measurements of the electro-polymeric film, a freshly prepared layer on a clean GCE was measured by centering the electrode surface area on the cleaned ATR-crystal.

The AM1-semiempirical computational level in Gaussian 03 W software was used to model phenols and the formed polymers molecular systems, and also to predict their IR-vibrational normal modes. The predicted models and IR-Spectra were visualized and presented by ChemDraw and Chem3D ultra, respectively, using ChemOffice Ultra 2006, version 10 from Cambridge Software, UK.

The following examples are set forth in assisting the invention and should not be construed as specifically limiting the invention described and claimed herein.

EXAMPLE 1

CV of 2-Chlorophenol and Pentachlorophenol Sodium Salt (pCP-Na)

Figure 1B:
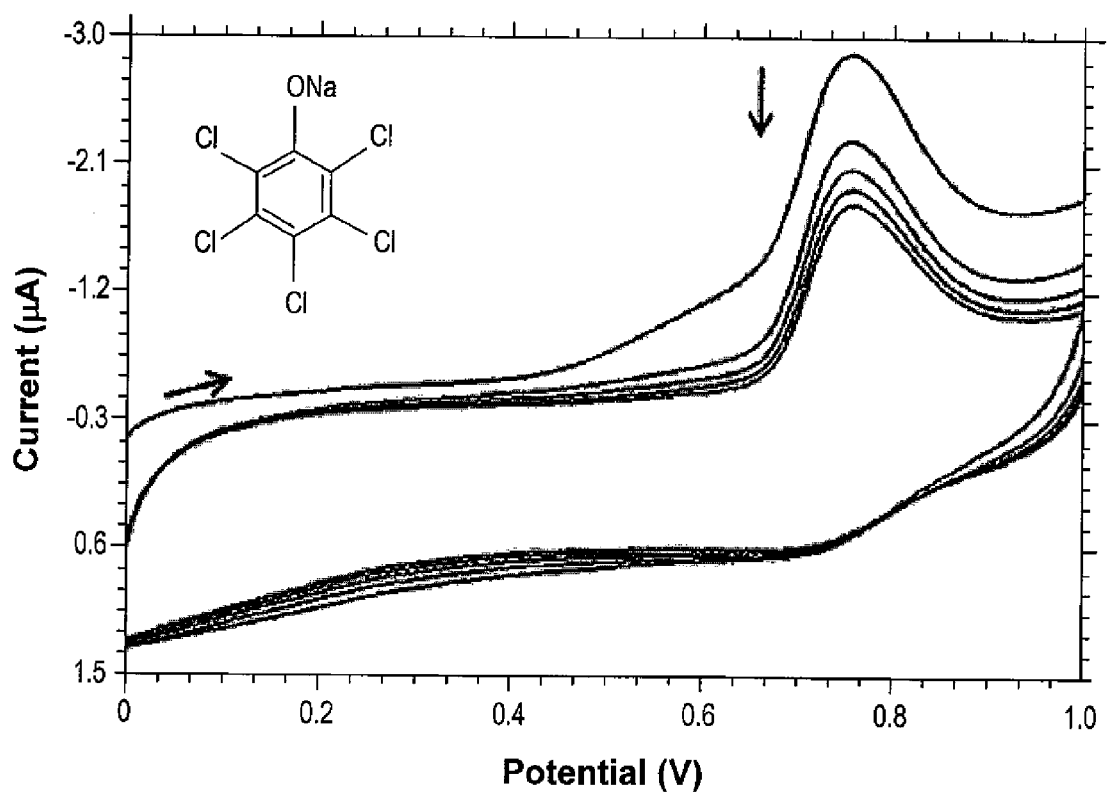
FIG. 1B is a cyclic voltammogram (CV) of five scans of pentachlorophenol sodium salt (pCP-Na salt, 30 µM) obtained in a phosphate buffer at (0.1 M, pH 7.0) at an accumulation potential of +400 mV, accumulation time of 60 seconds, and at a scan rate of 100 mV/s.

The electrode surface fouling effect and electropolymerization pathways of phenols were investigated using CV. As illustrated in FIG. 1A, the multiple cyclic voltammograms of chlorophenols (CPs) were investigated at the GCE surface. The results confirmed the presence of a "fouling effect" for the irreversible oxidation peak (Ep~650 mV), with the appearance, starting from the second cycle, of new reversible peaks appeared at lower oxidation potentials (Ep~+100 to +450 mV). A similar behavior is observed for all studied chlorophenols except pentachlorophenol sodium salt (pCP-Na) (see FIG. 1B), which does not produce any reversible peaks at all, indicating a relatively weak fouling effect.

EXAMPLE 2

SWASV of 2-Chlorophenol and Pentachlorophenol Sodium Salt (pCP-Na)

Figure 2A:
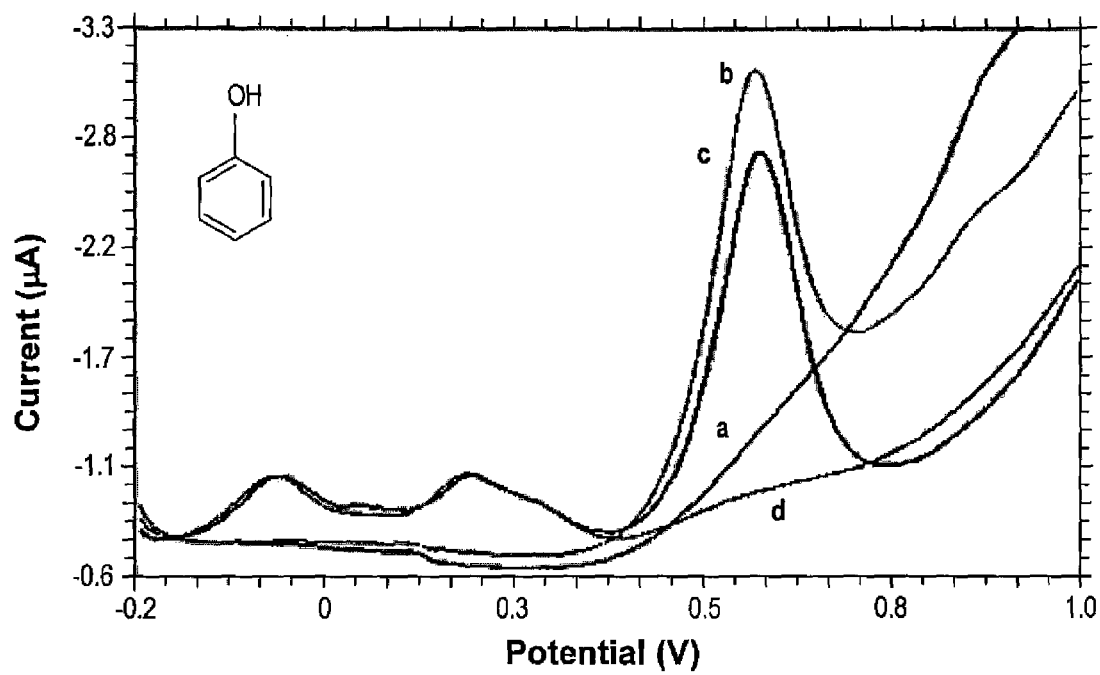
FIG. 2A is a square wave adsorptive stripping voltammogram (SWASV) of 30 µM phenol in a phosphate buffer (0.1 M, pH 9.0) for (a) blank (b) first scan (c) second scan without polishing and (d) subsequent third scan in a blank solution obtained at an accumulation potential of +0.4 V with an accumulation time of 60 s, amplitude 25 mV, pulse width, 8 mV and frequency, 15 Hz.
Figure 2B:
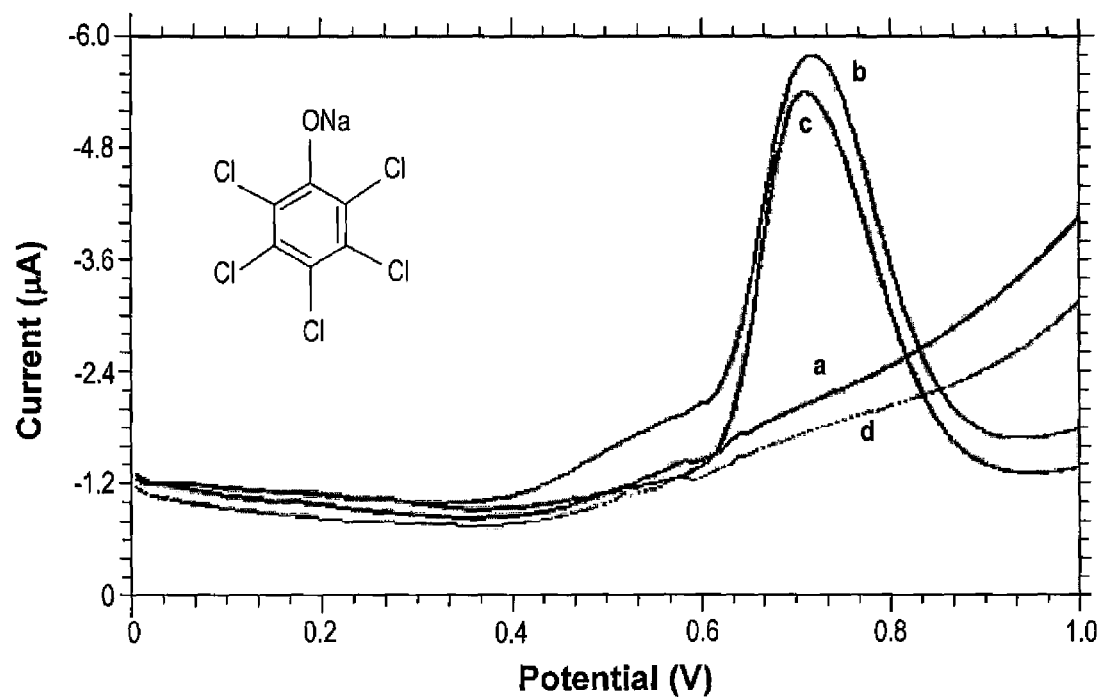
FIG. 2B is a square wave adsorptive stripping voltammogram (SWASV) of 30 µM pentachlorophenol sodium salt (pCP-Na salt) at pH 5 for (a) blank (b) first scan (c) second scan without polishing and (d) subsequent third scan in a blank solution obtained at an accumulation potential of +0.4 V with an accumulation time of 60 s, amplitude 25 mV, pulse width, 8 mV and frequency, 15 Hz.

In this example, the electrode surface fouling and electropolymerization pathways of phenols were investigated using SWASV. Electrochemical measurements were conducted in 0.1M phosphate buffer solution using a GCE. Representative results of typical SWASVs of phenol and pCP-Na are shown in FIGS. 2A & 2B. The mechanical polishing for the electrode surface between consecutive scans apparently helped in obtaining same peak current/area of FIG. 2b. On the other hand, the unpolished surfaces show ~10% lowering on that oxidation peak current and the appearance of new peaks at relatively lower oxidation potentials (FIG. 2A, c). Such peaks do not appear in case of pCP-Na (FIG. 2B, c). The lowering in the primary oxidation peak is attributed to the formation of a passive layer at the electrode surface, while the appearance of the new peaks is attributed to the formation of ortho- and para-izomerization products.

Figure 3A:
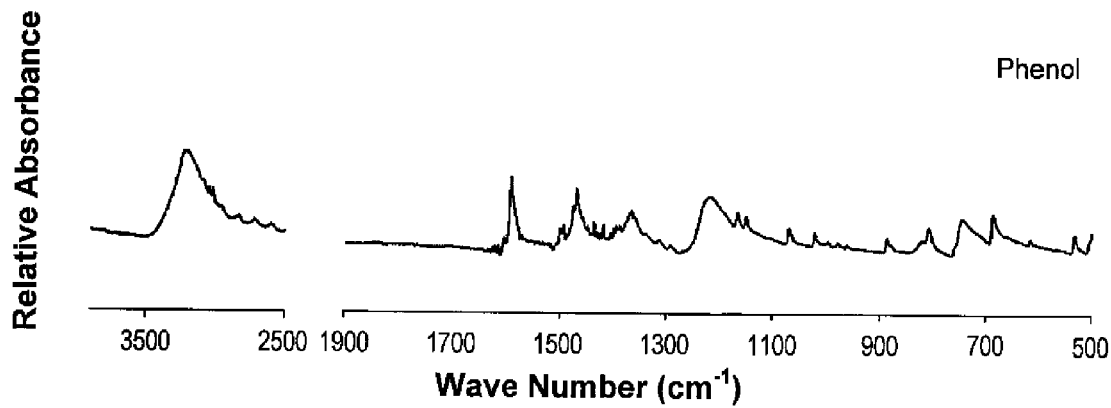
FIG. 3A is the FT-IR spectra of phenol using attenuated total reflectance (ATR)-Smart Orbit setup of Nicolet 6700-FTIR spectrometer.
Figure 3B:
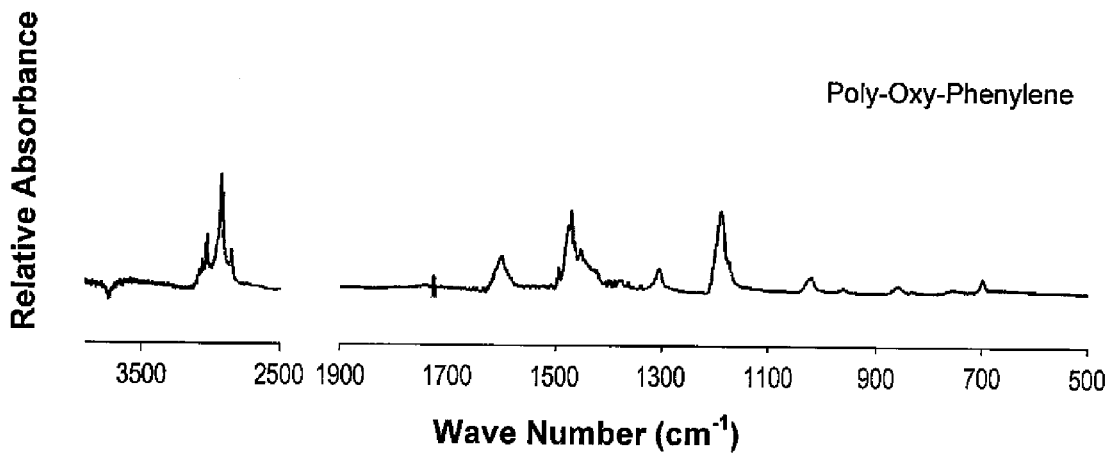
FIG. 3B is the FT-IR spectra of poly-oxy-phenylene using attenuated total reflectance (ATR)-Smart Orbit setup of Nicolet 6700-FTIR spectrometer.
Figure 3C:
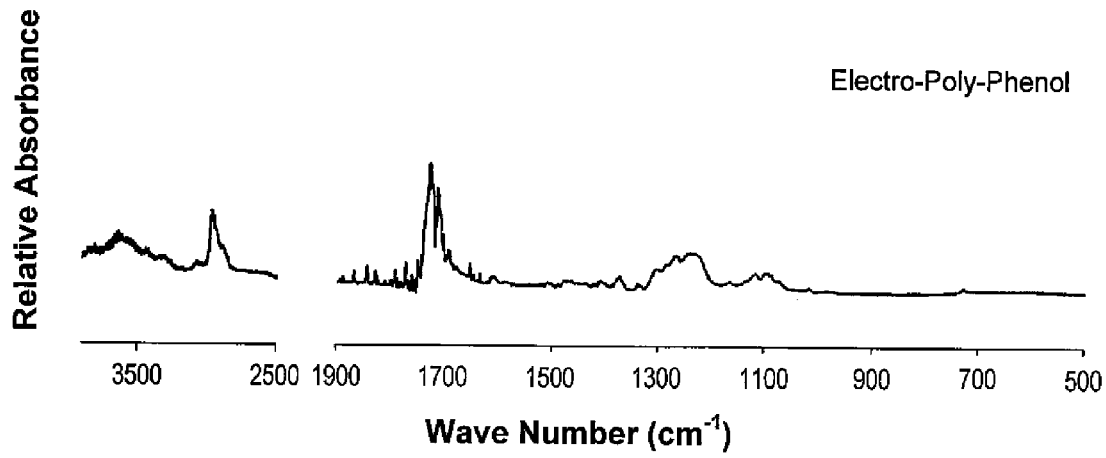
FIG. 3C is the FT-IR spectra of an electro-polymerized phenol using attenuated total reflectance (ATR)-Smart Orbit setup of Nicolet 6700-FTIR spectrometer, the electrochemical conditions for forming the electro-polymerized phenol being an accumulation potential of +400 mV with an accumulation time of 60 seconds and at a scan rate of 100 mV/s.

As shown in FIG. 3, the nature of the film produced in the SWASV scan of Example 2 was identified by obtaining its FT-IR spectra and comparing it with that of phenol and poly-oxy-phenylene polymer. The FT-IR spectrum of poly-oxy-phenylene as illustrated in FIG. 3b is similar to that of phenol as shown in FIG. 3a except for the appearance of C—O—C stretching band at around 1200 cm$^{-1}$ and the disappearance of the C—O—H broad band at about 1250 cm$^{-1}$. On the other hand, the electro-polymer phenolic film vibrational spectra is distinguished by the appearance of C=O and broad C—O—H stretching bands at about 1700 cm$^{-1}$ and 1250 cm$^{-1}$, respectively, and the disappearance of the aromatic C=C stretching bands within the range 1500-1600 cm$^{-1}$. These results indicate that the oxy-polymerization, mostly, did not exist at the electrode surface, and the new electro-active polymer contains ketonic as well as alcoholic hydroxyl functional groups.

Earlier mechanistic studies of the electro-oxidation of various phenol derivatives have proposed that the polymerization of phenolic compounds should happen at the ortho and para positions. Further study has proved that the most energetically favored routes of phenol polymerization should lead to carbon-carbon coupling through ortho-para and ortho-ortho links. Therefore, AM1-semiemprical calculation has been utilized in the present invention to predict the IR-normal vibrational modes of a proposed ortho-ortho coupled model of polymeric phenol as shown in FIG. 4 (bottom models and spectra) and then compare these modes with the corresponding values of a phenol molecular model (FIG. 4, top models and spectrum). This model is characterized with the presence of both ketonic and alcoholic functional groups.

The predicted FT-IR spectra of this model polymer indicated that the formation of the polymer is accompanied with the disappearance of the C=C stretching bands within the range 1500-1700 cm$^{-1}$ and the appearance of the C=0 and C=C vinyl alcohol stretching bands at higher wavenumbers within the range 1700-2100 cm$^{-1}$, respectively. At the same time, these ranges match with the experimental results (FIG. 3) with applying the recommended scaling of the computed frequencies using uniform correction factor of 0.92 for non-H stretches. These results support the experimental FT-IR results of the electro-polymerization products (FIG. 4c) and support the following polymerization pathways of phenol as shown in Scheme 1.

As depicted by Scheme 1, in these pathways, the phenolate anion oxidizes to phenoxy radical that isomerizes to ortho- and/or para-radical intermediate for addition-polymerization propagation steps. This is followed by para-ortho and/or ortho-meta coupling reactions to produce non-aromatic polymeric molecular systems that are characterized by vinyl-ketone and vinyl-alcohol functional groups. The presence of such functional groups, especially the vinyl-alcohol group, correlates well with the observed reversible redox behavior of the polymeric film which could be attributed to different hydroquinone-quinone redox-reaction process.

EXAMPLE 3

CV of Hydroquinone

Figure 5:
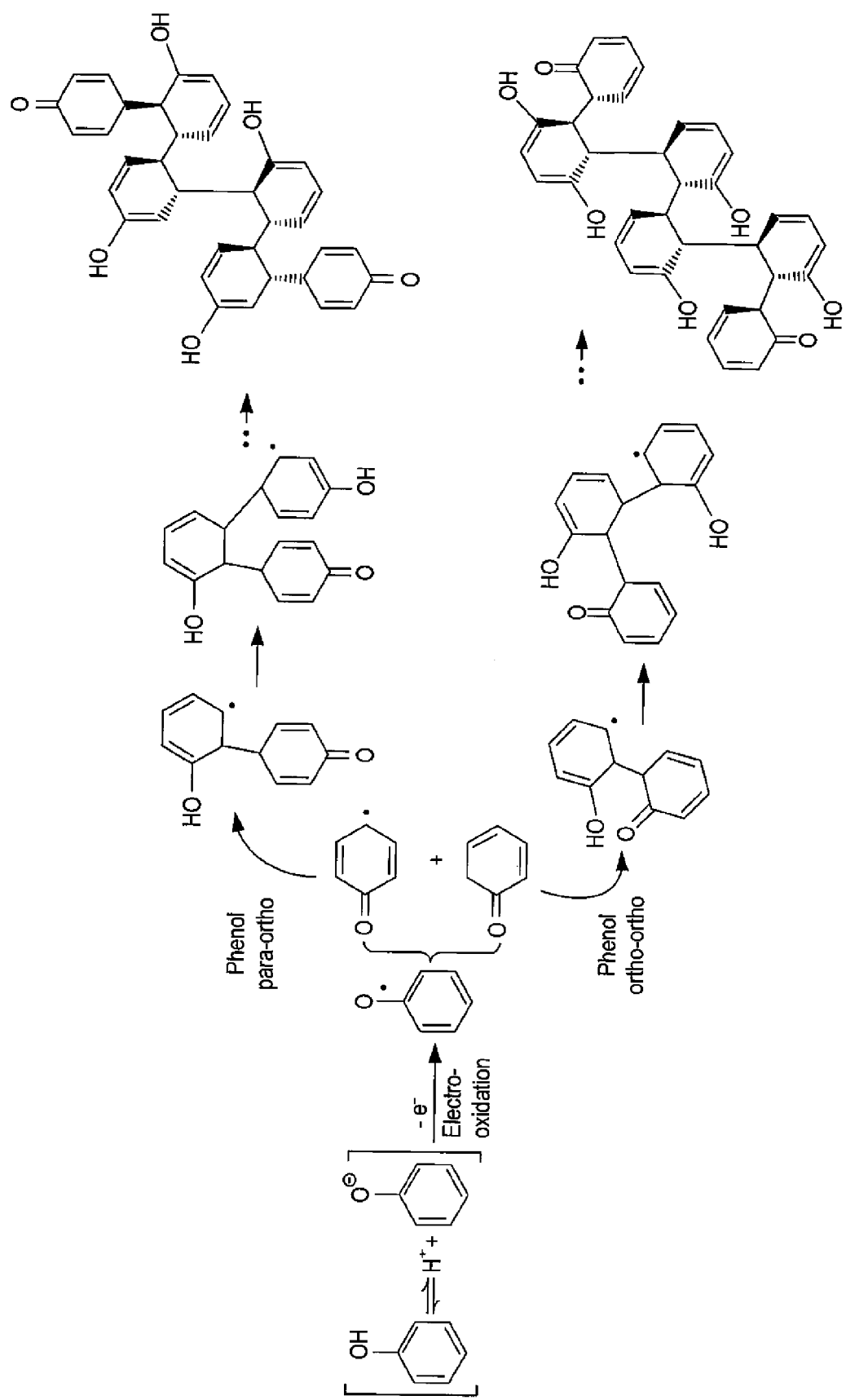
FIG. 5 is a schematic diagram of the polymerization reaction pathway of phenol and model compounds of the proposed para-ortho and ortho-ortho carbon-carbon coupling model compounds using AM1-semiemprical calculation.

The hydroquinone redox reaction was investigated with CV with GCE as the working electrode in phosphate buffer (0.1 M, pH 7.0) at an accumulation potential of +0.40 V, accumulation time of 60 and at a scan rate of 100 mV/s. The hydroquinone-quinone reaction process was confirmed by recording CV-voltammograms of hydroquinone. As shown in FIG. 5, the CV of hydroquinone produced a reversible redox-peak within the potential range of the redox peaks of the phenol polymer. Scheme 1 shows the possibility of the generation of different intermediate radicals to produce different phenol polymer conformers and explains the appearance of multi-redox peaks within the hydroquinone-quinone voltage range as shown previously in FIGS. 1 and 2. This was illustrated by a careful investigation of these redox peaks for different chloro-phenol derivatives. Chloro-derivatives were selected because the chlorine atom is classified as the least reactive halogen atom in the elimination processes of the electropolymerization reaction of phenols.

EXAMPLE 4

SWASV of (a) Phenol, (b) 2-CP, (c) 2,6-DCP, (d) 2,4-DCP, (e) 2,4,6-TCP, (f) pCP

Figure 6:
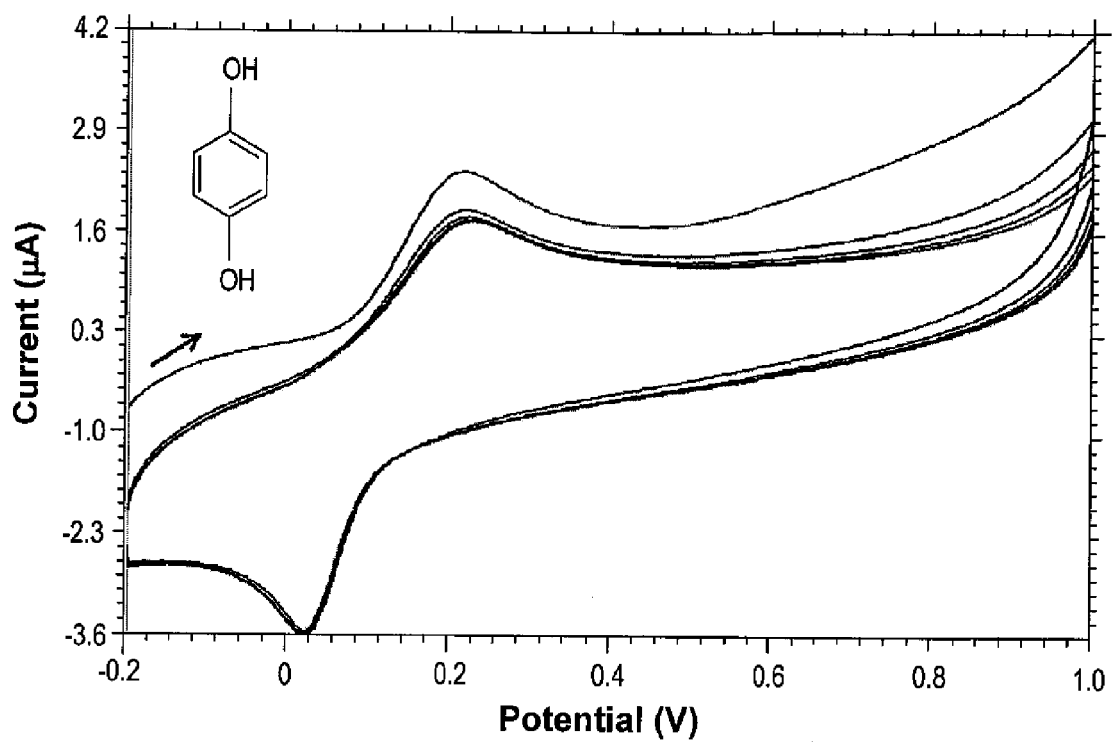
FIG. 6 is a cyclic voltammogram (CV) of five successive scans of 60 µM of hydroquinone obtained in phosphate buffer (0.1 M, pH 7.0) at an accumulation potential of +400 mV, accumulation time of 60 seconds and at a scan rate of 100 mV/s.
Figure 7:
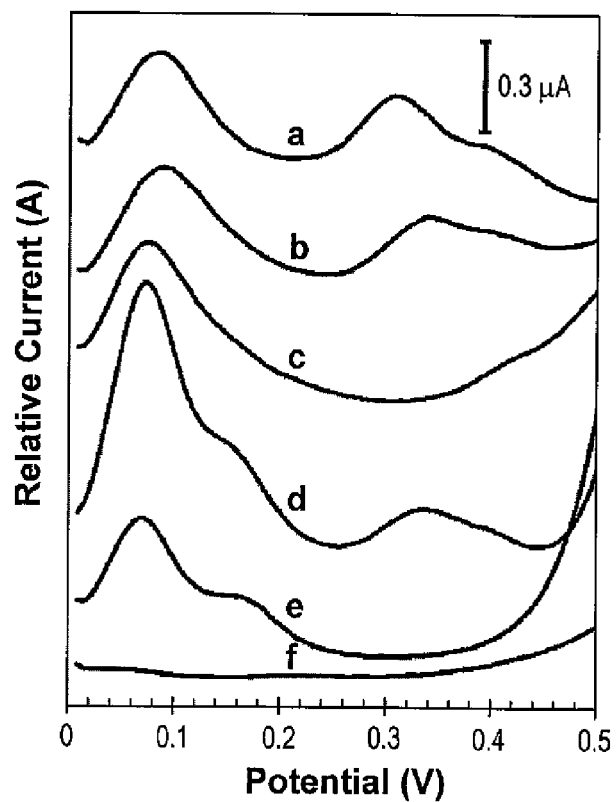
FIG. 7 shows square-wave absorptive stripping voltammogram (SWASV) scans without mechanical polishing of a glassy carbon electrode (GCE) in 0.1 M phosphate buffer for 30 µM of (a) phenol, (b) 2CP, (c) 2,6-DCP, (d) 2,4-DCP, (e) 2,4,6-TCP (f) pCP Na obtained at an accumulation potential of +0.4 V at an accumulation time of 60 s, amplitude 25 mV, pulse width 8 mV and frequency 15 Hz.

SWASV scans were conducted without mechanical polishing of GCE in 0.1 M phosphate buffer for 30 µM of (a) phenol, (b) 2-CP, (c) 2,6-DCP, (d) 2,4-DCP, (e) 2,4,6-TCP (f) pCP Na at an accumulation potential of +400 mV at an accumulation time of 60 s, amplitude 25 mV, pulse width 8 mV and frequency 15 Hz. The results of the second SWASV scans, as shown in FIG. 6, indicate that the blocking of some phenyl-position with chlorine atoms limits the number of the phenol polymer conformers and in turn leads to the disappearance of some of the redox-peaks or even the disappearance of all of them as in the case of pCP-Na salts (FIG. 7, scan f). This is confirmed by the disappearance of the +300 mV peaks when the ortho-positions were entirely blocked, as in the case of 2,6-dichlorophenol (26 dCP) and 2,4,6-trichlorophenol (2,4,6-tCP), (FIGS. 6c and 6e). FIG. 6e depicting the second scan of 2,4,6-tCP shows that an electroactive polymer film exists on the electrode surface even though all ortho- and para-positions are blocked. This demonstrates that the meta-meta carbon-carbon coupling is possible, which could be due to the presence of the meta-carbon in a position in between three chlorine atoms, two of them at ortho- and another one at para-positions.

The assumption of the dependency of the electro-oxidation of CP's on the phenolate anion formation in Scheme 1 was investigated by studying the pH dependence of the oxidation pathways of phenols at +400 mV accumulation potential for 60 sec in pH range 5.00-9.00 of 0.1 M phosphate buffer solutions. The SWASV-voltamograms of phenol indicated that the electro-oxidation potential shifts toward less positive potential as the pH increases. Identical behavior was observed for all CPs except pCP-Na salt, which did not show any shift. In general, a direct relation is found to exist between the current/area of the oxidation peaks of phenol and chloro-phenol derivatives and their corresponding concentrations of the phenolate anions, [A$^-$].

As shown in Table 1, the results indicate that the phenolate anions [A$^-$] in these processes is moving towards an optimum value within the range of 1-5 µM, which was predicted from the corresponding pKa values. The phenolate concentrations [A$^-$] at values other than optimum give lower oxidation current/peak areas, which is obvious at concentrations lower than the optimum value.

TABLE 1

The Optimum [A$^-$] and electrodecomposition potentials (Ep) of studied phenols

| Analyte | pH | $E_P$(mV) | $pK_a$ | [A–] (µM) |
|---|---|---|---|---|
| Phenol | 9.0 | 626 | 10.0 | 3.00 |
| 2-Chlorophenol | 7.0 | 652 | 8.29 | 1.54 |
| 2,4-Dichlorophenol | 7.0 | 625 | 8.09 | 2.44 |
| 2,6-Dichlorophenol | 6.0 | 644 | 6.79 | 4.87 |
| 2,4,6-Trichlorophenol | 5.0 | 614 | 6.29 | 1.54 |

For the values that are higher than the optimum, the lowering could be attributed to the possible phenolate radical scavenging competition reaction.

EXAMPLE 5

SWASV of 2CP (2-Chlorophenol)

Figure 8A:
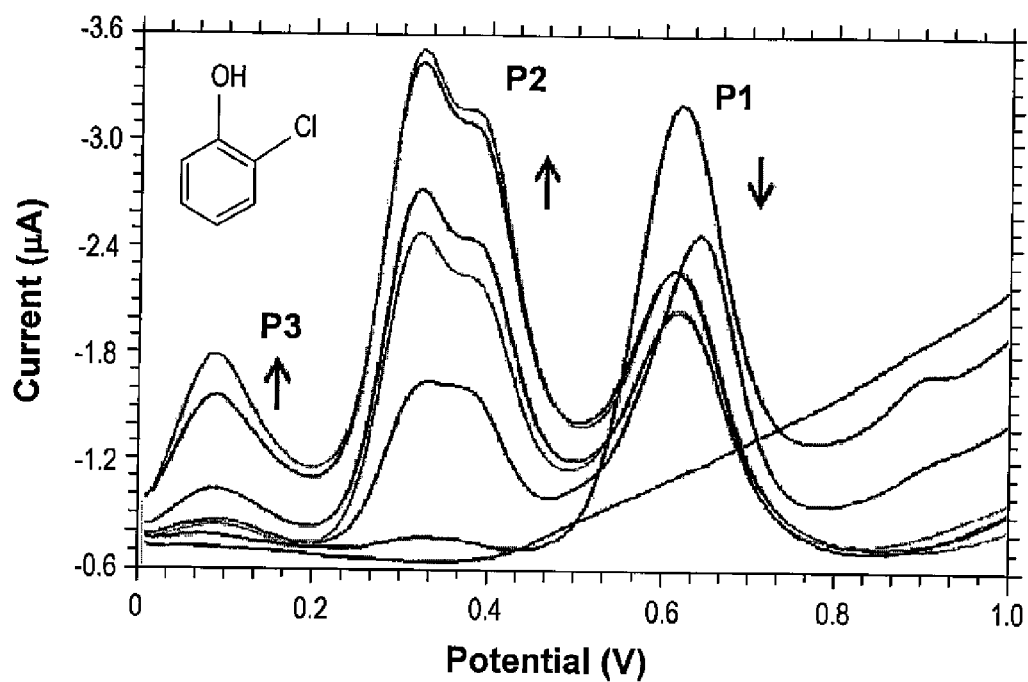
FIG. 8A shows SWASV scans for 2-chlorophenol (30.0 µM) with different accumulation potentials ranging from +100 mV to +1200 mV on a GCE.
Figure 8B:
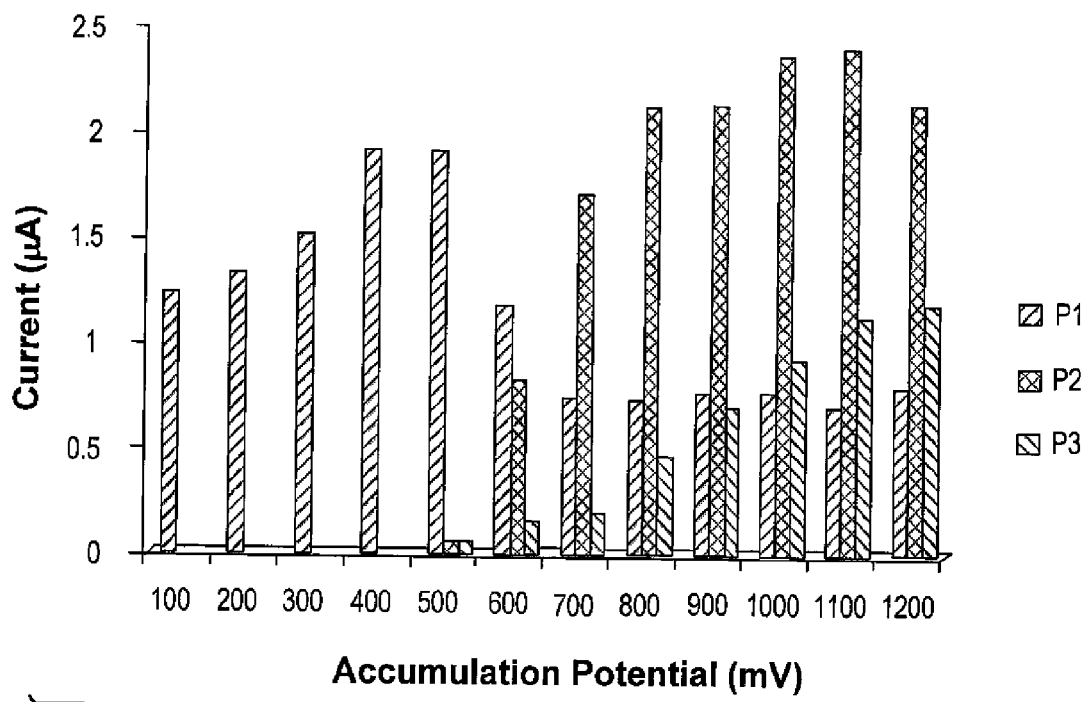
FIG. 8B shows the corresponding histograms for the P1, P2 and P3 peak heights of the SWASV scans of FIG. 8A.

SWASV of 2-chloropenol (30.0 µM) was conducted at GCE working electrode. FIG. 8A shows the accumulation potential effect on the oxidation peak of 2-chlorophenol (2CP) using SWASV with different accumulation potentials ranging from +100 mV to +1200 mV on GCE. FIG. 8B shows the corresponding histogram for P1, P2 and P3 peak heights. The result shows that accumulation potential of phenols helps in obtaining three peaks at a single scan. As the accumulation potential increases, the current magnitude of the first anodic oxidized peak (P1, Ep~+600 mV) decreases while the peaks for 2CP-polymer film (P2, Ep ~+300 mV and P3, Ep~+100 mV) dramatically increases. Systematic investigation of the accumulation potential effect as shown in FIG. 8B indicates that P1 is the only obtained peak, which increases up to +400 mV before it starts to be reduced and level off around +700 mV. From +500 mV, the observed reduction in P1 is accompanied by the appearance of the redox-active polymeric film's peaks, P2 and P3, that increase subsequently with the increase of the accumulation potential applied value. At approximately +800 mV accumulation potential, the sensitivity of P1 signal is overtaken by P2 signal. The obtained results prove that the peak 2 (P2) is very promising and even competing with the conventional P1 for possible analytical determination of CPs.

A comprehensive study to obtain the optimum electrochemical parameters of peak 1 (P1, accumulation potential at +400 mV) and peak 2 (P2, accumulation potential at +1100 mV) of 2 CP was performed at the corresponding optimum pH value of phosphate buffer solution (0.1 M). A summary of these optimum parameters for both peaks is tabulated in Table 2.

TABLE 2

Optimum conditions for Peak 1 (P1) and Peak 2 (P2) of 2CP

| 2CP | pH | Acc. Pot. | Acc. Time | Frequency | Amplitude | Increment |
|---|---|---|---|---|---|---|
| P1 | 7.00 | +400 mV | 60 s | 100 Hz | 50 mV | 8 mV |
| P2 | 5.00 | +1100 mV | 60 s | 100 Hz | 100 mV | 8 mV |

As evidenced by the results of Table 2 and FIG. 7, electrochemical optimization of P2 results in a complete disappearance of the primary oxidation peak, P1. This phenomenon could be attributed to the formation of a highly compact polymer film on the GCE electrode surface that completely prevents the penetration of phenol molecules from the bulk to the electrode surface.

The obtained optimization parameters in Table 2 for both peaks were used to conduct the electroanalytical determination of 2 CP and construct the corresponding calibration curves.

EXAMPLE 6

SWASV of 2CP (2-Chlorophenol)

SWASV of 2-chlorphenol were performed at +400 mV accumulation potential for 60 seconds for the following concentrations: (a) 0.0 μM, (b) 5.0 μM, (c) 10.0 μM, (d) 25.0 μM, (e) 35.0 μM, (f) 40.0 μM, (g) 50.0 μM, (h) 55.0 μM, and (i) 60.0 μM. (SWASV) of 2-chlorphenol were performed at an accumulation potential of +1100 mV for 60 s for the following concentrations: (a) 0.0 μM, (b) 1.0 μM, (c) 2.0 μM, (d) 3.0 μM, (e) 4.0 μM, (f) 5.0 μM, (g) 6.0 μM, (h) 7.0 μM, (i) 9.0 μM and 0) 11.0 μM.

Figure 9A:
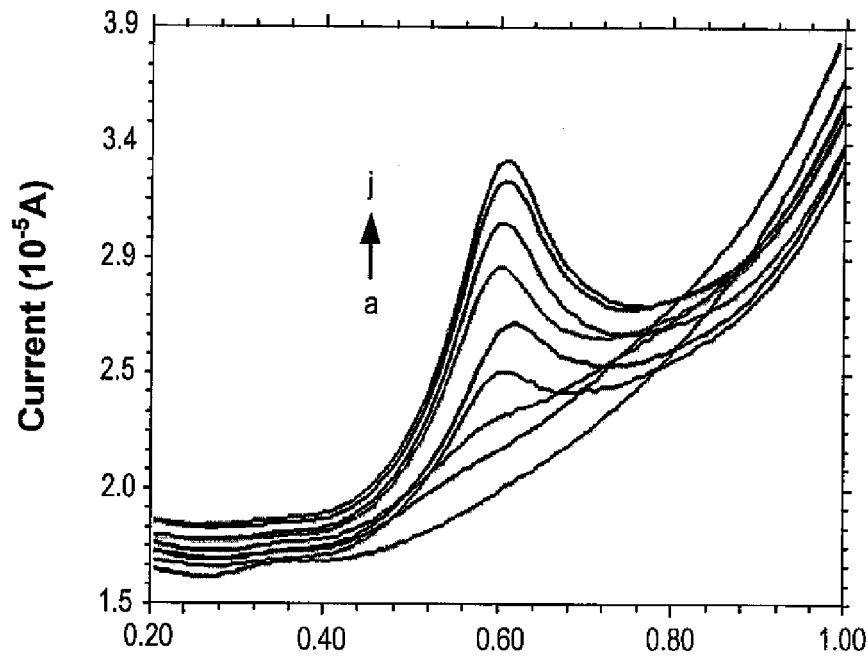
FIG. 9A shows SWASV scans of 2-chlorophenol at +400 mV accumulation potential for 60 sec for the following concentrations: (a) 0.0 µM, (b) 5.0 µM, (c) 10.0 µM (d) 25.0 µM, (e) 35.0 µM, (f) 40.0 µM, (g) 50.0 µM, (h) 55.0 µM, and (i) 60.0 µM.
Figure 9B:
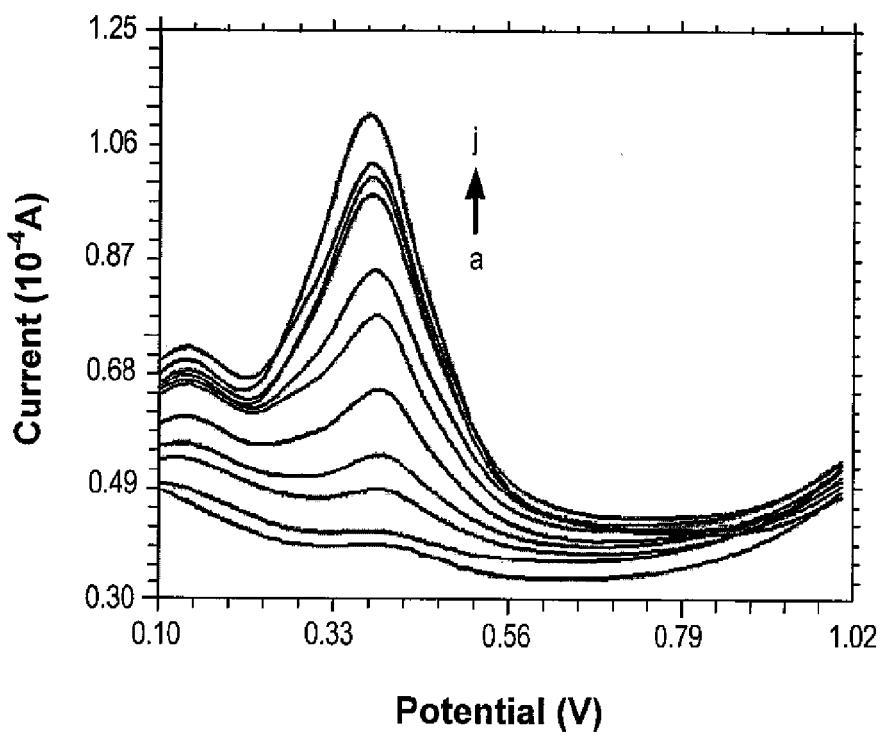
FIG. 9B shows square SWASV scans of 2-chlorophenol at an accumulation potential of +1100 mV for 60 seconds for the following concentrations: (a) 0.0 µM (b) 1.0 µµM, (c) 2.0 µM, (d) 3.0 µM, (e) 4.0 µM, (f) 5.0 µM, (g) 6.0 µM, (h) 7.0 µM, (i) 9.0 µM and 0) 11.0 µM.

FIG. 9 illustrates the voltammograms of 2-CP for concentration ranges from 5.0 to 60 μM (FIG. 9A), and 1.0 to 11 μM (FIG. 9B). Each voltammogram was obtained using a mechanically polished electrode surface.

Figure 10:
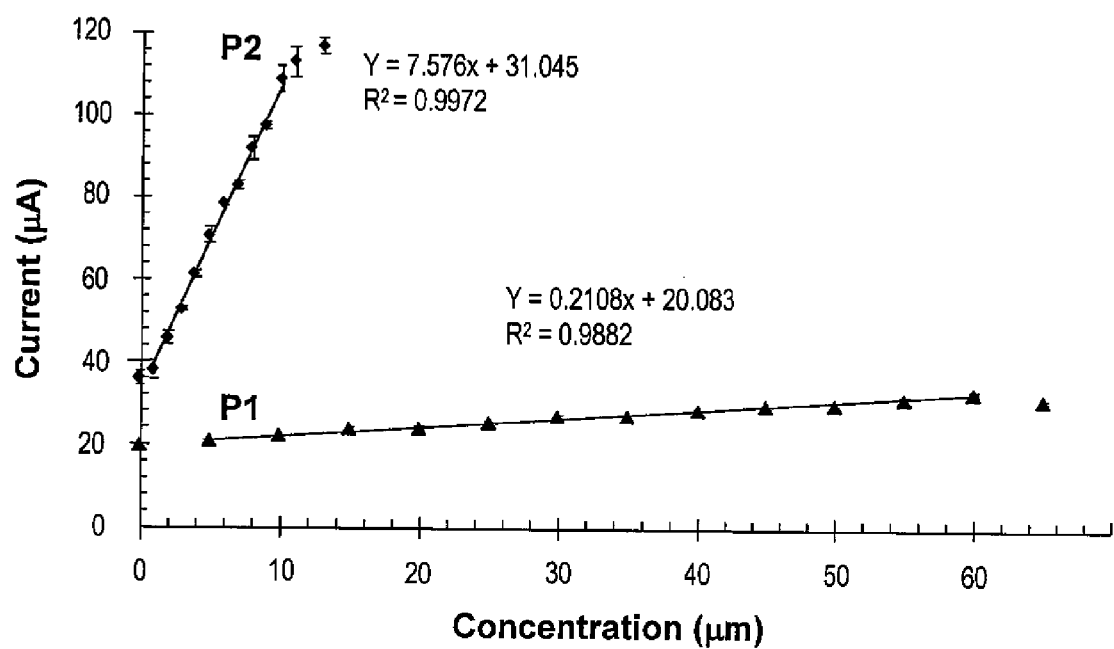
FIG. 10 is a plot comparing the linear regression and calibration of peak 1 (P1) obtained at an accumulation potential of +400 mV against peak 2 (P2) of the redox polymeric film obtained at an accumulation potential of +1100 mV.

FIG. 10 shows the linear regressions, sensitivity and limit of detections (LOD) as obtained from the linear equations of the straight lines for P1 and P2. Surprisingly, over 35-fold increase on the sensitivity is achieved via monitoring P2 (slope, 7.576±0.135 A mol$^{-1}$) versus P1 (slope, 0.211 ±0.007 A mol$^{-1}$). Such dramatic improvement on the sensitivity is accompanied by 10-fold on the calculated analytical detection limit. According to the IUPAC rigorous definition, the detection limit is the concentration that produces a current significantly different from the background current value by at least three standard deviations of the blank. The calculated detection limits for peak 1 (P1) and peak 2 (P2) were 3.81 μM (960 ppb) and 0.36 μM (91 ppb) respectively. Moreover, the analytical performance of both peaks was investigated for seven repeated measurements of the same concentration (30.00 μM). The relative standard deviation for P1 is 1.31%, and it is 1.84% for P2.

The present method proposes reaction pathways of phenol polymerization via free radical addition reactions to form para-ortho and/or ortho-meta carbon-carbon coupled polymers. As discussed above, the pentachlorophenol sodium salt (pCP Na) did not form any polymers due to the absence of exchange protons (H) in the benzene ring. This clarifies the misconception reported in the prior art that pentachlorophenol does not passivate, i.e., "foul" the surface of glassy carbon electrode (GCE). With the influence of the accumulation potential, new peaks appeared along with the irreversible conventional anodic peak of phenols. Therefore, by electroanalytical optimization of the new peaks at the potential range of 0 to 500 mV, the present method unexpectedly achieves a 35-fold greater sensitive analytical method for detection of phenolic compounds such as 2-chlorophenol and other chloro-derivatives. Hence, the present method illustrates that the formed phenolic polymer oxidation peaks provides a more sensitive electroanalytical method of detecting phenols and its derivatives.

It is to be understood that the present invention is not limited to the embodiments described above, but encompasses any and all embodiments within the scope of the following claims.

We claim:

1. An electroanalytical method for determination of phenols, comprising the steps of:
    contacting an aqueous sample of a phenolic compound with an electrode assembly having a working electrode;
    determining a response of the working electrode in a voltammogram by varying a potential applied to the working electrode, wherein the potential applied to the working electrode is an accumulation potential during a square-wave adsorptive stripping voltammetry measurement, the square-wave adsorptive stripping voltammetry measurement being conductive at a pulse amplitude of 25 mV with a pulse width of 8 mV and at a frequency of 15 Hz;
    measuring the size of peaks in the voltammogram corresponding to a redox-active polyphenol film that develops at the working electrode at an electro-polymerization potential of the phenolic compound in order to determine the concentration of the phenolic compound.

2. The electroanalytical method according to claim 1, further comprising the steps of:
    preparing calibration curves for the redox-active polymeric film voltammogram peaks for known concentrations of the phenolic compound; and
    extrapolating the measured size of the sample's voltammogram peaks against the calibration curve to determine the concentration of the phenolic compound in the aqueous sample.

3. The electroanalytical method according to claim 1, wherein said electrode assembly further comprise a counter electrode, a reference electrode, a voltage supply to said working and counter-electrodes and a current meter for determining the current between said working and counter-electrodes.

4. The electroanalytical method according to claim 3, wherein the counter electrode is a platinum wire electrode and the reference electrode is Ag/AgCl.

5. The electroanalytical method according to claim 1, wherein the working electrode is an unmodified glassy carbon working electrode.

6. The electroanalytical method according to claim 1, wherein the redox-active polymeric film displays characteristic peaks at oxidation potentials in the range from +0.0 V to 450 mV.

7. The electroanalytical method according to claim 1, wherein the phenolic compound is selected from the group consisting of phenol, chlorophenol and derivatives thereof.

8. The electroanalytical method according to claim 1, wherein the phenolic compound is phenol.

9. The electroanalytical method according to claim 1, wherein the phenolic compound is chlorophenol.

10. The electroanalytical method according to claim 1, wherein the detectable corresponding peaks in said voltammogram increase with an increase in value of the accumulation potential.

11. The electroanalytical method according to claim 1, wherein determining the response of said working electrode in a voltammogram comprises measuring and recording the current generated from the sample.

* * * * *